United States Patent [19]

DiMaggio, Jr. et al.

[11] 4,413,584
[45] Nov. 8, 1983

[54] BIOLOGICAL SLIDE STAINING APPARATUS

[75] Inventors: Joseph P. DiMaggio, Jr., Bergenfield; Henry Eng, Clifton; Donald A. Ball, Warren; Kenneth J. Walenciak, Wayne, all of N.J.

[73] Assignee: A.J.P. Scientific, Inc., Clifton, N.J.

[21] Appl. No.: 269,079

[22] Filed: Jun. 2, 1981

Related U.S. Application Data

[63] Continuation-in-part of Ser. No. 897,884, Apr. 19, 1978, Pat. No. 4,274,359.

[51] Int. Cl.$^3$ .................. B05C 11/12; B05C 13/02
[52] U.S. Cl. .................................. 118/56; 118/64; 118/326; 118/501
[58] Field of Search .............. 427/4; 422/50, 68; 118/64, 315, 56, 326, 500, 501

[56] References Cited

U.S. PATENT DOCUMENTS 4,274,359  6/1981  DiMaggio et al. .............. 118/56

Primary Examiner—Bernard D. Pianalto
Attorney, Agent, or Firm—David A. Jackson

[57] ABSTRACT

An apparatus for staining biological slides comprises a support housing; a slide conveyor assembly mounted within the support housing and including a slide support tray for holding a plurality of biological slides; a stain dispensing assembly within the support housing, having a plurality of dispensers adapted to be located above the slide support tray; and a stain removal assembly located within the support housing adjacent the dispensers, and including a fluid drain and a fluid evaporator. The slide tray is manually inserted and removed from the support housing, and is adapted to hold the slides throughout the entire staining process to minimize slide damage. Only two fluids, a stain and a buffer, are required and the entire procedure may be completed within seven minutes.

9 Claims, 7 Drawing Figures

BIOLOGICAL SLIDE STAINING APPARATUS

CROSS-REFERENCE TO RELATED APPLICATION

The present application is a continuation-in-part of copending application Ser. No. 897,884, filed Apr. 19, 1978, by the Inventors herein now U.S. Pat. No. 4,274,359.

BACKGROUND OF THE INVENTION

1. Field of the Invention

The present invention relates to an apparatus for the staining of biological slides, and particularly to a slide staining apparatus which may automatically process a plurality of such slides.

2. Description of the Prior Art

In the biological arts, and particularly in the field of medical technology, the investigation of living tissues and fluids for structure and possible pathology has long proceeded with the aid of microscopic investigation. Specifically, samples of tissues and fluids have classically been placed upon small rectangular glass plates, known as slides, which are then placed under a microscope or similar magnifying device where visible structural characteristics may be viewed. In connection with microscopic investigations, the employment of staining compositions developed to aid in the identification process. At the inception, slides were manually treated and stained prior to viewing, however, particularly in the area of medical technology, the great numbers of slides that required staining for viewing in critical disease investigations was inadequate. To this end, those in the art sought to develop methods and associated apparatus of the automatic staining of a plurality of slides.

A machine for the automated multiple staining of slides is presently available which employs a conveyor-type transporting arrangement, whereby the slides are placed on the conveyor and are sequentially indexed past stations for the dispensing of stain composition, buffer, and then rinse solution. This machine is employed in the area of blood sample evaluation, where the parameters of time and volume are most critical. Though it is an improvement over manual staining techniques, the machine suffers from certain defects of operation. Specifically, the slide is locked in position once it is placed on the conveyor and cannot be removed until the entire staining cycle is completed; thus, individual slides could not be removed for special attention. Further, the slides are stained in serial order and, frequently suffer from non-uniform staining due to excess dispensing of the stain composition components at the respective stations. Finally, the mechanism comprising the conveyor frequently causes jamming of slides with resulting delays in slide movement, which itself may contribute to overstaining of a particular sample, and which generally delays the staining process for all slides presently on the machine.

In our parent Application Serial No. 897,884, the disclosure of which is incorporated herein by reference, a biological slide staining apparatus is disclosed that utilizes a slide tray defining a plurality of seats for biological slides to rest upon. The slide tray is inserted into the machine in the horizontal position and may be removed at any time, for example, to retrieve a particular slide. The machine includes a stain dispenser assembly with a plurality of spigots located above the slides when inserted, which are connected to reservoirs for stain, buffer and rinse solutions via one or more fluid pumps. Sequential application of the respective solutions is electronically controlled. A stain removal means comprises fluid drains, a fan and a heater that first removes excess liquid from the sample, and then circulates warm air to fully dry the stained sample. The slide tray comprises an outer frame and inner slide shelf that is adapted to pivot vertically about one end to urge excess fluid to run off.

The closest prior art known to applicants was made of record during the prosecution of Ser. No. 897,884 and is as follows:

U.S. Pat. No. 2,400,315—Paasche;
U.S. Pat. No. 3,053,223—Hensen, et al.

The present invention is directed to certain modifications of applicants' earlier apparatus, that are believed to confer improved speed and efficiency of operation.

SUMMARY OF THE INVENTION

An apparatus for staining biological slides is disclosed which comprises a support housing, a slide conveyor assembly mounted within the support housing including a slide tray adapted to hold a plurality of slides in parallel position adjacent to each other and to reciprocate into and out of said support housing, a dispensing assembly disposed above said conveyor assembly including a plurality of dispensing spigots, for dispensing the slide staining compositions on the slides, said spigots mounted in said support housing so as to reside in overhead relation to said support tray when said support tray is fully received within said support housing and a stain removal assembly located within said support housing, for removing excess stain composition and drying said slides.

The slide support tray of the present invention comprises a generally rectangular outer frame containing an aperture within which nest paired inner shelf members, adapted to support a plurality of biological slides in parallel relation to each other. Each shelf member is capable of pivoting upward in relation to said frame and in opposite direction to the other in order to facilitate the rapid drain off of excess stain composition from the slides.

The apparatus of the present invention is characterized by ease of operation and accuracy of staining, as the slide samples are subjected to the various staining sequences while at one station. Thus, all of the dispensing spigots for the respective components of the staining solutions are located together above the respective slides, rather than at spaced locations or stations. Further, employment of manual conveyance of the slides to the staining station in the apparatus of the present invention eliminates the possibility of jamming or other malfunction which frequently leads to inaccuracies in staining and damage to the slide samples.

Accordingly, it is a principal object of the present invention to provide an apparatus for the staining of biological slide samples which is easily and rapidly operated with reduced incidence of failure.

It is a further object of the present invention to provide a slide staining apparatus which employs manual slide mounting and removal without detriment to reduced staining time.

It is a yet further object of the present invention to provide a slide staining apparatus as aforesaid which facilitates the simultaneous, independent staining of a plurality of slides.

DETAILED DESCRIPTION OF THE INVENTION

Figure 1:
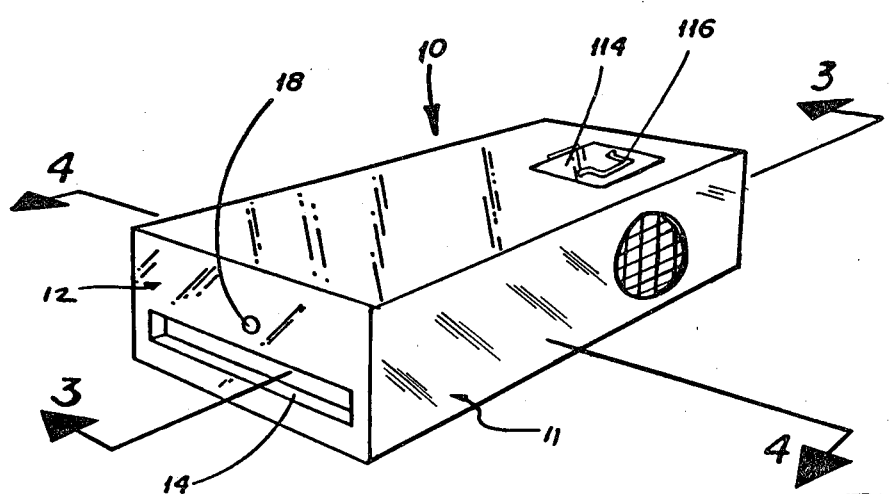
FIG. 1 is a perspective view illustrating the general outer appearance of an apparatus in accordance with the present invention.

Referring to the drawings, wherein like numerals designate like parts, FIG. 1 illustrates the outer appearance of the slide staining apparatus of the present invention. Thus, apparatus 10 comprises a support housing 11 that is rectangular in shape and provides, at its front face 12, a large rectangular mouth 14 which comprises the point of insertion of a slide support tray as will be further described below.

Referring further to FIG. 1, indicator light 18 is shown which signals the operation of slide staining apparatus 10. Further, when the slide staining procedure is terminated the indicator light will extinguish to advise that the staining procedure is over.

The foregoing illustration is general and should not be viewed as limitative of the appearance of face 12, as additional indicia, lights, switches and the like may be provided with variations in model features.

Figure 2:
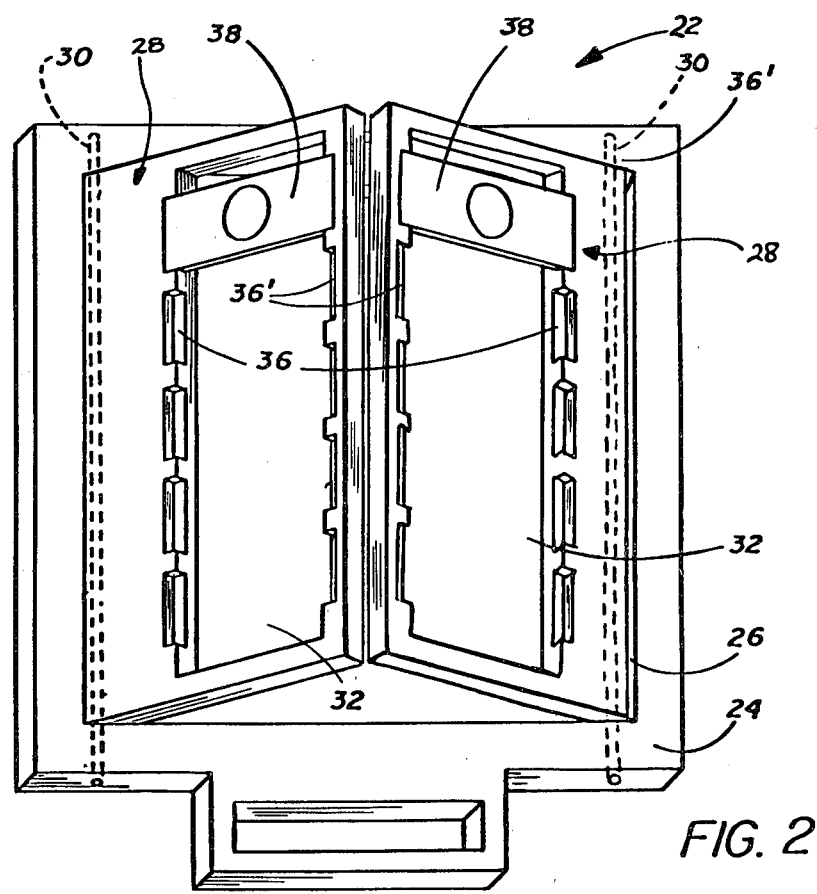
FIG. 2 is a top perspective view partly in phantom showing the slide support tray of the present invention in one of its operative positions.

Referring now to FIG. 2, the slide support tray 22 is shown in perspective to illustrate the manner of operation.

Tray 22 comprises a generally rectangular outer tray frame 24 which defines a generally rectangular aperture 26 within which paired, centrally located slide shelves 28 may be situated. Slide shelves 28 are adapted for pivoting movement in relation to frame 24 by the placement of axles 30 shown in phantom, journaled through both shelves 28 and the adjacent portions of frame 24 as illustrated. Slide shelves 28 are mounted in the same manner as double doors, and are adapted to pivot upward as shown, and in opposite directions to each other. As will be described hereinbelow, the pivoting movement of slide shelves 28 enhances the drying of the slides, as it facilitates the runoff of excess stain composition, and assists the rinse cycle, described later on.

Slide shelves 28 define parallel rectangular openings comprising major openings 32. Openings 32 are provided with paired recesses 36 and 36' which comprise seats for situation of the slides therein. Thus, before inserting support tray 22 into mouth 14, one places a plurality of slides such as slides 38 in communication with paired recesses 36 and 36', where they will reside until the staining process is completed.

Slide support tray 22 is loaded by placing a number of slides bearing biological slide samples within recesses 36 and 36' so that the samples are horizontal and face upward. After loading, slide support tray 22 is then inserted into mouth 14 of support housing 11 and is then pushed as far as possible until residing within the positions illustrated in FIGS. 3 and 4.

Figure 3:
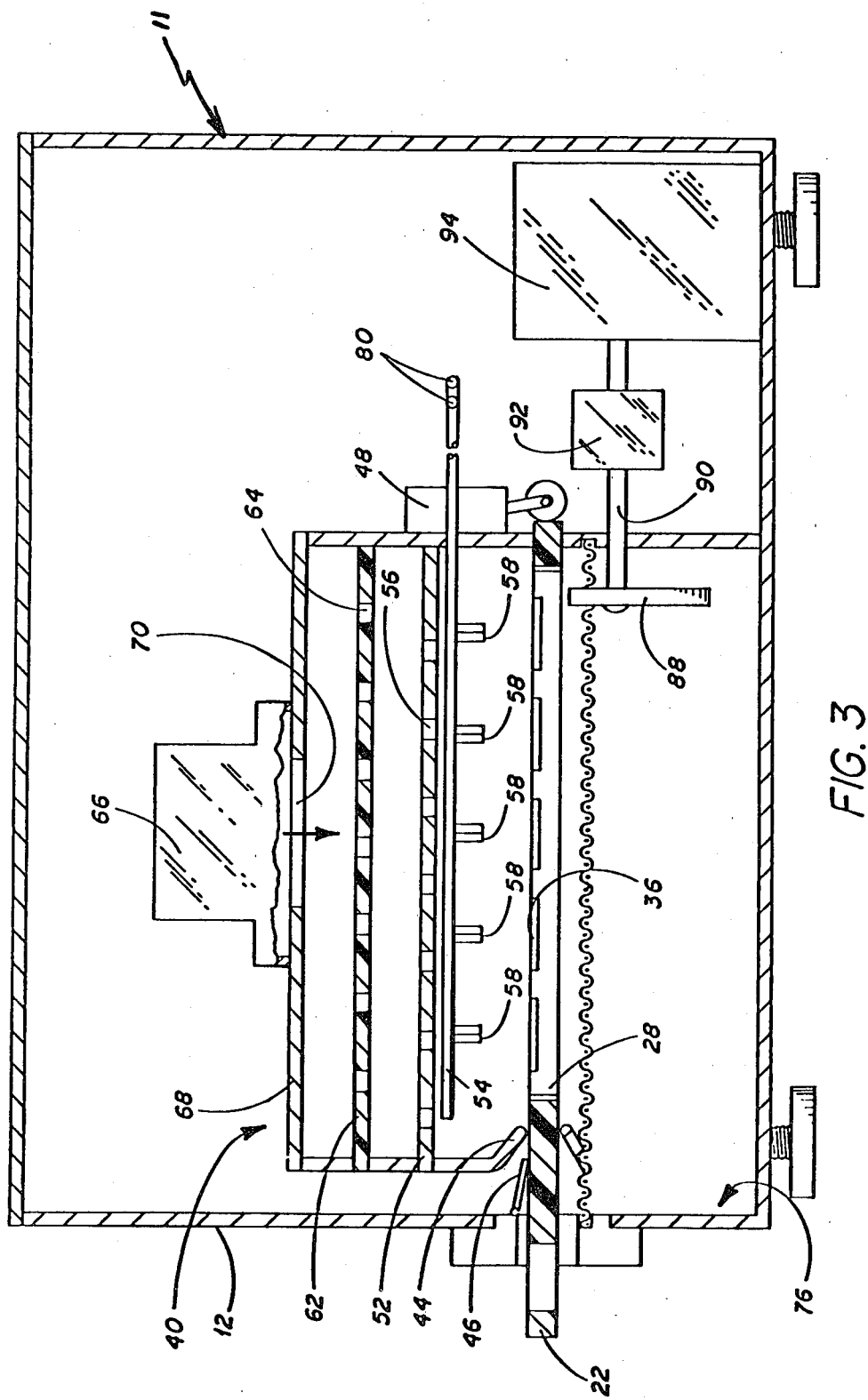
FIG. 3 is a side sectional, partly schematic view taken through line 3—3 of FIG. 1 further illustrating the apparatus of the present invention.
Figure 4:
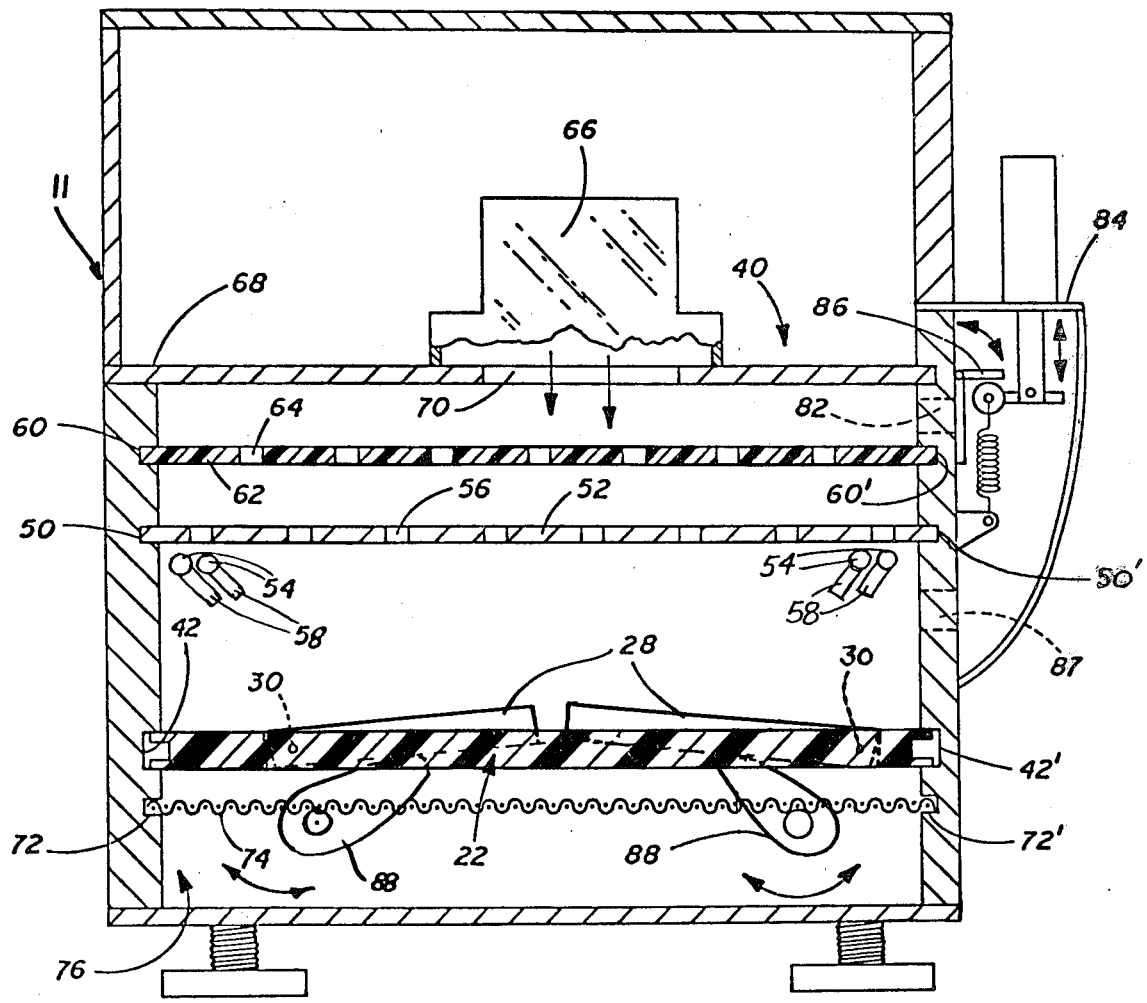
FIG. 4 is a front sectional view of the apparatus of FIG. 1 taken through line 4—4.

In FIG. 3, slide support tray 22 is fully inserted within support housing 11, and is held by slide conveyor assembly 40 within tracks 42 and 42' as illustrated in FIG. 4. Conveyor assembly 40 is mounted within support housing 11 and includes slide support tray 22 and a plurality of tracks 42 and 42' for its slidable reception and support. Conveyor assembly 40 may include a beveled entrance 44 that communicates with mouth 14 in facing 12 to assist in guiding slide support tray 22 on insertion. Also, a pivotable door 46 may be mounted at mouth 14 as a dust guard which can move upward and out of the way when slide tray 22 is inserted, but will normally reside in the closed position. A pressure switch 48 may be provided at the rear of conveyor assembly 40 to activate the staining sequence after it is depressed by slide tray 22.

Conveyor assembly 40 as illustrated in FIG. 4 may be an essentially rectangular structure and may define a plurality of spaced apart, parallel tracks for the insertion and support of a plurality of structures to be located in overhead relation to slide support tray 22. Specifically, tracks 50 and 50' may be provided directly above tracks 42 and 42' to engage a diffuser plate 52 which in one embodiment may support the stain composition dispensing manifolds 54 that are a part of the stain dispensing assembly. Diffuser plate 52 forms a part of the stain removal assembly, discussed later, and is provided with a plurality of perforations or apertures 56 to permit air to flow through to assist in drying slides 38.

Referring further to FIG. 4, a third pair of tracks 60 and 60' may be provided above tracks 50 and 50' to receive baffle plate 62, which serves in a manner similar to diffuser plate 52 to permit air to circulate downward and over slides 38 after excess stain composition has been removed. Thus, baffle plate 62 also defines a plurality of baffle plate apertures 64 which permit the air to pass therethrough.

Referring again to FIG. 4, one further set of tracks 72 may be provided below slide support tray 22 to retain screen 74. Screen 74 is provided to catch a slide 38 should it slip out of position on slide shelf 28 at any time during the staining sequence.

While conveyor assembly 40 is shown with the additional tracks for the removable reception of the diffuser plate, the baffle plate and the screen, these parts may be directly mounted within support housing 11. The invention should not, therefore, be limited to the particular construction illustrated.

The present staining apparatus includes a stain dispensing assembly located within support housing 11. The stain dispensing assembly includes a plurality of dispensers comprising dispensing manifolds 54, located above the portion of conveyor assembly 40 that receives slide tray 22.

Figure 5:
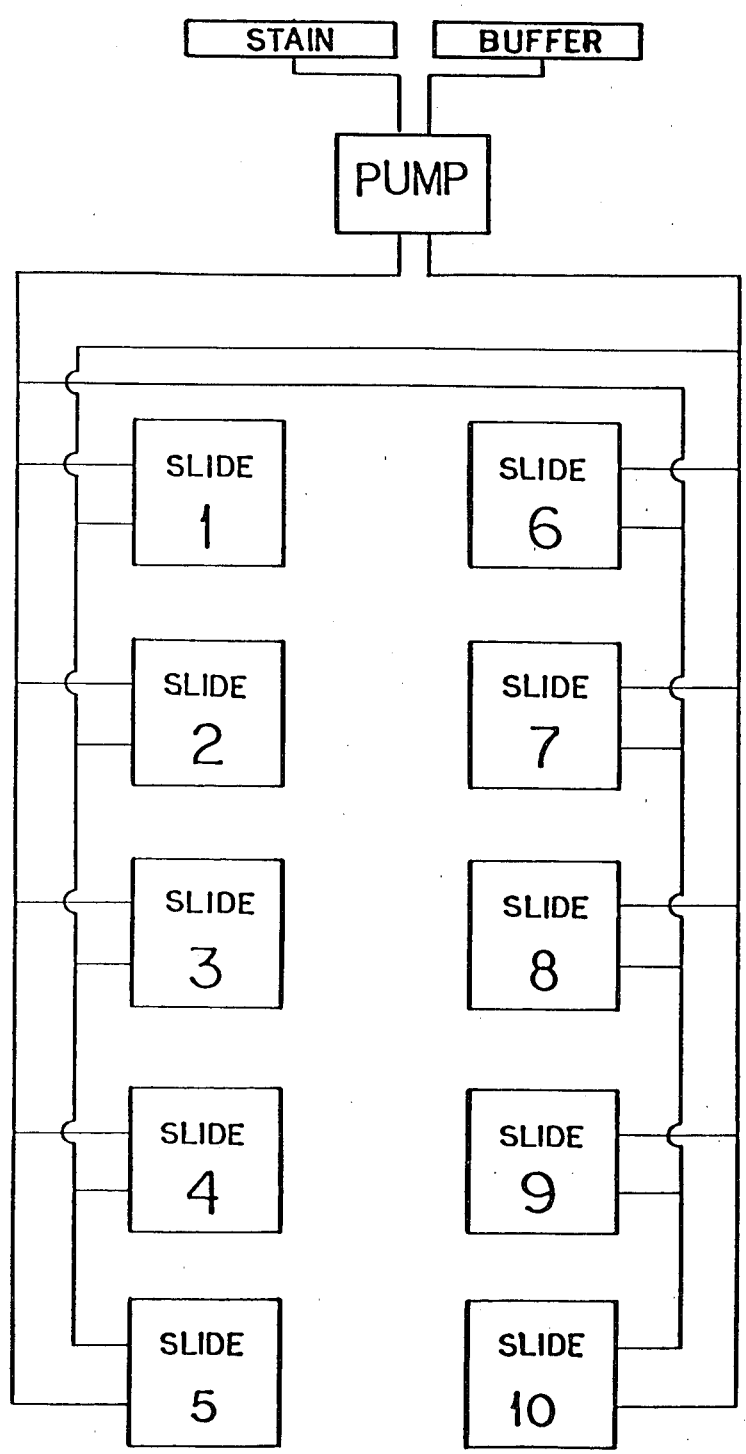
FIG. 5 is a schematic flow diagram illustrating the dispensing means of the apparatus of the present invention.
Figure 7:
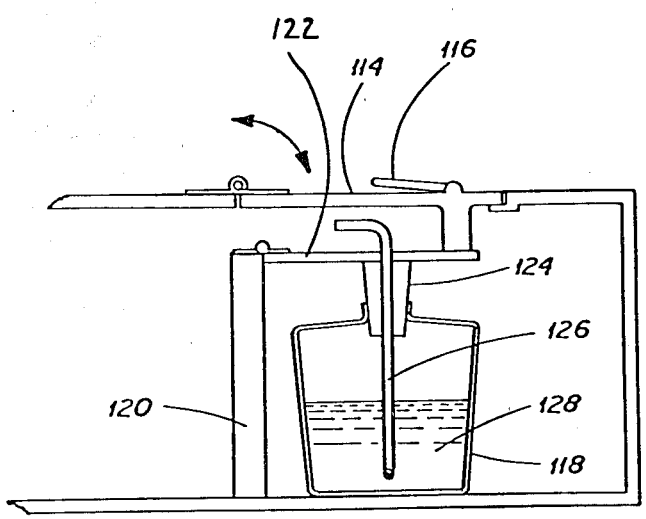
FIG. 7 is a side sectional, partly schematic view illustrating the reservoirs that may be employed in accordance with the present invention.

Referring also to the flow chart of FIG. 5, dispensing manifolds 54 receive the respective staining solutions from one or more pumps, which in turn, are fluidly connected to solution reservoirs. Both the pumps, not otherwise shown, and the reservoirs, one of which is shown in FIG. 7, may be mounted within support housing 11, in a location that would be accessible for maintenance, and the exact location of these elements is not a critical aspect of the invention.

Dispensing manifolds terminate at their dispensing end in a plurality of dispensing spigots 58 that may, as illustrated, extend upwardly from the manifolds and then turn downward in the direction of the location of the samples on the slides, to insure that the staining compositions will be dispensed directly thereon. The upward extension of spigots 58 is provided to preclude the leakage of unwanted staining composition after the stain and rinse solution dispensing cycles terminate.

Referring again to FIGS. 4 and 5, the apparatus of the present invention operates with the application of two solutions to the slide sample, and therefore, each bank of slides disposed on a separate shelf 28 can be serviced by two manifolds 54, each manifold having a number of spigots 58 corresponding to the number of slides 38 on each shelf. As illustrated herein, each shelf 28 may carry five slides, and therefore each manifold 54 defines five spigots 58. Naturally, the number of spigots 58, as well as the slide capacity of slide tray 22 may vary within the scope of the invention. Further, the number of manifolds 54 may correspond to the embodiment described in our earlier application, referred to earlier and incorporated herein by reference.

Apparatus 10 also includes a stain removal assembly, that is likewise located within support housing 11 adjacent conveyor assembly 40. A fluid drain component comprises a first element of the stain removal assembly, and is provided to coact with the slide tray 22 to assist in the removal of excess staining compositions from the surface of each slide. Referring to FIGS. 3 and 4, at least one and preferably two motor activated lift cams 88 are situated below slide tray 22 and are pivotable into contact with the undersides of shelves 28 to urge them into the inclined position shown in FIG. 4, to aid fluid runoff. Cams 88 may be connected to each other by appropriate gear linkage, not shown, or may be individually linked by a cam shaft 90 to a timing gear assembly 92, actuated by a motor 94, all illustrated schematically herein. The exact sequence of cam actuation may be electronically preset, so that shelves 28 are raised and then lowered after the fluid has been dispensed. The exact timing of cam movement may be adjusted to provide, if desired, an interval of delay after the application of the staining fluid. The provision of an adjustment capability is contemplated within the scope of the invention.

The fluid drain component also includes a sump or drain 76 defined by the bottom or floor of support housing 22 to collect staining fluid that runs off as described above. Drain 76 may be attached to an appropriate external drain, such as an industrial sink by a conduit, not shown, that would extend from the bottom of support housing 11.

The stain removal assembly includes a fluid evaporator component that, as mentioned earlier, removes any moisture remaining on the slide sample and fully dries the slide. The fluid evaporator component may include a blower 66, shown herein mounted on a support plate 68, that operates to direct a current of air past the slides. One or more air barriers, such as baffle plate 62 with its baffle plate apertures 64, and diffuser plate 52 with its apertures 56, amy be interposed between blower 66 and slide tray 22. The air barriers distribute the air currents evenly to prevent sample damage during drying. Also, blower 66 may include a heating element, not specifically illustrated, to provide heated air to hasten the evaporation of the staining composition.

OPERATION

The staining apparatus 10 is employed by first placing a number of slides 38 within the recesses 36 and 36' of a slide support tray 22 that is outside support housing 11. Slide support tray 22 is then inserted into mouth 14 and thrust forward until the leading edge of tray frame 24 engages the end of tracks 42 and 42'. As illustrated, a pressure switch 48 may be positioned so that full insertion of slide support tray 22 causes switch 48 to activate the apparatus. In the instance where manual activation is desired, switch 48 is absent, and the operator activates the apparatus by external switching means.

The present invention includes a new method of staining slides that requires the employment of only two solutions, namely, the stain and the buffer. Thus, the stain may be directly applied to the slides to provide the appropriate coloration to the sample to make certain artifacts visible for microscopic examination. The stain employed in the present method may be applied without the preliminary treatment of the sample with a fixative, and this reduction in solutions and procedures confers its corresponding economies.

In the present method, the buffer is employed as the rinse as well, so that while three fluid application steps are performed, only two different solutions need be stored and dispensed.

Figure 6:
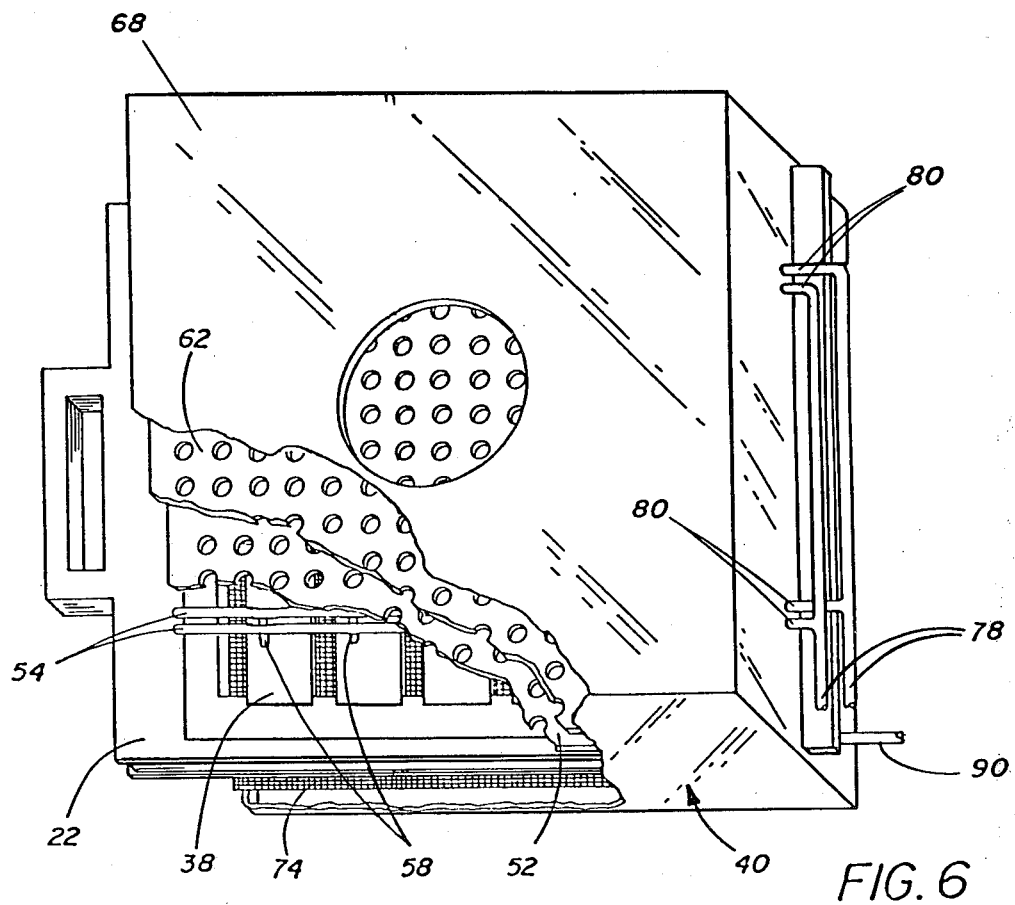
FIG. 6 is perspective view partly broken showing yet another view of the present invention.

Referring now to FIG. 5, a flow diagram schematically representing the apparatus of the present invention illustrates the placement of the aforementioned two components of the stain composition in individual containers or reservoirs which are then drawn by means of the pump as illustrated for purpose of dispensing via manifolds 54 and spigots 58. The application of the components of the stain composition as described above must take place sequentially with the application of the stain being the first step. Accordingly, the pump schematically disclosed in FIG. 5 must draw from each of the reservoirs set forth above in sequence; that is, the stain must initially be applied, after which the buffer is dispensed over the slide sample for both the buffer and rinse cycles. Thus, each of the primary lines exiting the pump is divided into two secondary lines each terminating in a manifold 54. The relationship of the primary lines, secondary lines and manifolds can be visualized by reference to FIG. 6 comprising a broken perspective view showing the two primary lines 78 splitting into four secondary lines 80 which may then enter the rear of conveyor assembly 40 to become manifolds 54. Each of the manifolds 54 provides, as disclosed earlier, a dispensing spigot 58 for the purpose of dispensing the particular solution over each of the respective slides 38.

In accordance with the foregoing, the first composition applied to the slidea comprises the stain, followed by the buffer. Referring to FIG. 3, the slide shelf 28 remains in the horizontal position illustrated in FIG. 3 during the application of the stain and buffer. Also, during this time, blower 66 is activated and directs a gentle stream of air over the slides to assist in the mixing of the two components. The air stream must be relatively gentle so as not to drive the components away from the sample, or to otherwise disturb proper staining.

Control of blower pressure may be achieved by a variety of means, such as by electric motor speed control. A vent assembly may be included, as illustrated, and may comprise secondary air channel 82 shown in FIG. 4 mounted between support plate 68 and buffer plate 62. Air channel 82 could be automatically opened by the action of solenoid 84 on L-shaped pivotable door 86 responsive to the commencement of the staining sequence. As soon as the buffer application sequence is completed, solenoid 84 would be released causing door 86 to spring back into closed position, to enable blower 66 to exert full pressure on the samples. The inclusion of the vent assembly is for purposes of illustration herein, and not limitation.

In conjunction with the application of full blower pressure as set forth above, the completion of the application of the buffer solution to the slides signals the commencement of the rinsing and drying sequence. It is at this time that slide shelf 28 is urged into the upward canted positioned illustrated in FIG. 4 by the action of lift cams 88, positioned distally with respect to axles 30 holding shelves 28 in position within frame 24. As described earlier, cams 88 are operatively connected to motor 94, and respond to a preset electronically timed sequence. Upon the rotation of cams 88 into the position shown in FIG. 4, the rinse application of the buffer solution is made via spigots 58 to the slides to facilitate the removal of the stain and buffer solutions therefrom.

After the completion of the rinse cycle, blower 66 continues to exert a high pressure stream of air against the slides to drive off the excess stain composition which, as discussed with respect to FIG. 2, passes between the slides 38 and is collected within sump 76. Drying continues to completion signalled by a moisture sensor, not shown, whereupon a signal indicator such as a light is activated.

In general, the apparatus of the present invention operates through a staining cycle of approximately six minutes commencing with the insertion of slide tray 22 and ending with the signal that the slides are dry. Insofar as the insertion and removal of the slide tray is manually accomplished, the apparatus of the present invention is best described as providing for the semi-automated staining of biological slide samples. In distinction to the prior art devices described earlier, the present invention retains the slides in stationary position upon the slide tray throughout the sequence and thereby avoids the difficulties frequently encountered when the slides are caused to move through the apparatus during the application of the various stain compositions.

A portion of the apparatus of the present invention is provided for the placement of the stain composition reservoirs. Generally, such reservoirs are located at the rear of the apparatus, and may be directly accessible from the exterior of the apparatus in the manner illustrated in FIG. 7. Thus, outer housing door 114 is provided which may have a handle 116 for access to an inner compartment which holds the reservoir 118. Reservoir 118 is held in fixed stopper position by means of retainer 120, connected at one end thereof to the base of the apparatus and at the other end thereof to a hingable stopper assembly 122. Stopper assembly 122 comprises a planar member having a affixed to one side thereof a stopper structure 124. A Cannulus 126 is provided which passes through stopper assembly 122 and stopper 124 to contact the stain composition contained within the reservoir 118. Cannulus 126 extends in the other direction to the pump carrying the staining solutions to the manifolds 54.

A fresh reservoir 118 is easily secured within apparatus 10 by first opening door 114, then exerting upward tension on stopper assembly 122 to disengage stopper assembly 112 from the mouth of the spent reservoir. The spent reservoir 118 is then removed and replaced, and stopper assembly 122 is lowered into engagement with the mouth thereof. Cannulus 126 is made of a flexible material which prevent damage or breakage that may occur during this procedure. After stopper assemnly 22 is placed within the mouth of reservoir 118, door 118 is lowered into place where it can be seen that lock 130 located on the inner side of door 114 serves to firmly retain stopper assembly 122 in position within reservoir 118. Door 114 may be provided with a latch not shown which secures its engagement with the top of the housing of the apparatus of the present invention. The entire assembly for receiving the reservoirs is illustrative, as simple placement within apparatus 10 may be utilized.

While there have been herein shown and described the preferred embodiments of the present invention, it will be understood that the invention may be embodied otherwise than as herein specifically illustrated or described and that within said embodiment certain changes in the detail and construction, and the form and arrangement of the parts may be made without departing from the underlying idea or principles of this invention within the scope of the appended claims.

What is claimed is:

1. In an apparatus for staining biological slides comprising,
   a support housing,
   a slide conveyor assembly mounted within said support housing,
   a slide tray for holding a plurality of slides removably insertable into said support housing,
   a stain dispensing assembly disposed within said housing with a plurality of dispensers located to be above said slide support tray when said slide support tray is fully inserted into said support housing, and
   a stain removal assembly located within said support housing and adjacent said dispensers, said stain removal assembly including a fluid drain component and a fluid evaporation component;
   the improvement wherein said slide support tray consists essentially of:
   at least two slide shelves mounted along parallel, laterally opposed pivot axes enabling said slide shelves to rotate away from each other in the same plane, said pivot axes so positioned when said slide support tray is fully inserted in said support housing that said slide shelves are adapted to cooperate with said stain removal assembly to tilt upward in a plane transverse to the plane in which said slide support tray resides within said support housing.

2. The improvement of claim 1 wherein said conveyor assembly comprises at least one pair of parallel tracks adapted to slidably receive said support tray.

3. The improvement of claim 2 wherein said conveyor assembly comprises a plurality of paired, parallel tracks, provided to slidably receive a screen below said slide support tray, and at least one perforate air barrier thereabove.

4. The improvement of claim 1 wherein said slide support tray comprises an outer tray frame defining a central aperture therein, and paired slide shelves adapted to nest in edge abutment within said central aperture and pivotally attached to said tray frame along parallel edges thereof, and said slide shelves are adapted to pivot upward and out of the plane of said outer tray frame in oppositely directed arcuate paths from each other.

5. The improvement of claim 1 wherein each of said slide shelves defines a generally rectangular opening bordered on parallel sides by said seats, said rectangular opening provided to permit excess staining composition to run off said slide.

6. The improvement of claim 1 wherein said stain dispensing assembly comprises at least two paired fluid manifolds mounted above the location of said slide support tray within said support housing, a plurality of dispensing spigots extending periodically from the uppermost surface of said manifolds and directed at their open ends toward the locations for said slides on said slide support tray, each manifold defining spigots equal in number to the maximum number of slides supportable by said slide support tray.

7. The improvement of claim 6 wherein said dispensing assembly further includes a plurality of stain composition reservoirs, at least one fluid pump connected thereto, said fluid pump adapted to deliver said stain composition to said manifolds, said manifolds are individually provided for each of said reservoirs.

8. The improvement of claim 1 wherein the fluid drain component of said stain removal assembly comprises at least one cam member adapted to cause said slide shelves to tilt upward a generally rectangular opening in each of said slide shelves to assist in staining composition run off, and a drain defined by said support housing and disposed below said slide support tray to gather the run off staining composition.

9. The improvement of claim 1 wherein the fluid evaporator component of the stain removal assembly comprises an air blower mounted above said conveyor assembly, and at least one perforated air barrier located between said blower and said slide support tray when it is fully inserted within said support housing, to generate an evaporative stream of air uniformly distributed over the slides to remove any remaining moisture therefrom.

* * * * *